United States Patent
Amberg et al.

[11] Patent Number: 5,965,700
[45] Date of Patent: Oct. 12, 1999

[54] PREPARATION OF ACTIVE PEPTIDES

[75] Inventors: Wilhelm Amberg, Friedrichsdorf; Harald Bernard, Bad Dürkheim; Ernst Buschmann, Ludwigshafen, all of Germany; Andreas Haupt, Westborough, Mass.; Bernd Janssen; Ulrich Karl, both of Ludwigshafen, Germany; Andreas Kling, Mannheim, Germany; Stefan Müller, Römerberg, Germany; Kurt Ritter, Heidelberg, Germany; Thomas Zierke, Böhl-Iggelheim, Germany

[73] Assignee: BASF Aktiengesellschaft, Ludwigshafen, Germany

[21] Appl. No.: 08/983,460
[22] PCT Filed: Jul. 12, 1996
[86] PCT No.: PCT/EP96/03073
§ 371 Date: Jan. 13, 1998
§ 102(e) Date: Jan. 13, 1998
[87] PCT Pub. No.: WO97/05162
PCT Pub. Date: Feb. 13, 1997

[30] Foreign Application Priority Data

Jul. 28, 1995 [DE] Germany .............. 195 27 575

[51] Int. Cl.$^6$ .................................. A61K 38/08
[52] U.S. Cl. .............. 530/330; 530/331; 530/333; 530/338; 514/18; 514/19; 514/17
[58] Field of Search .................. 530/333, 330, 530/338, 331; 514/18, 19

[56] References Cited

FOREIGN PATENT DOCUMENTS 80 14195  1/1981  France .
93/23424  5/1993  WIPO .

OTHER PUBLICATIONS

Bodanszley, Int. J. Peptide. Prot. Res. 25, 449–474, 1985.
FEBS Ltrs. vol. 227, No. 2, 171–174, 1988.
Chem. Abst. vol. 115, 280575j, 1991.
Tet. vol. 48, No. 20, 4115–4122, 1992.
Monatshefte fur Chem. 109, 147–155, (1978).
J. Org. Chem. 1989, 54, 6005–6006.
J. Am. Chem. Soc., vol. 113, 6692, 1991.
Tet. vol. 50, No. 42, 12097–12108, 1994.

*Primary Examiner*—Johann Richter
*Assistant Examiner*—David Lukton
*Attorney, Agent, or Firm*—Keil & Weinkauf

[57] ABSTRACT

A process for preparing pentapeptides of the formula I

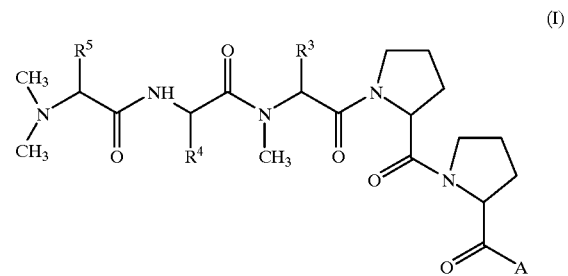

where A and $R^1$–$R^3$ have the stated meanings, comprises assembling the pentapeptide stepwise starting from a prolinamide of the formula II

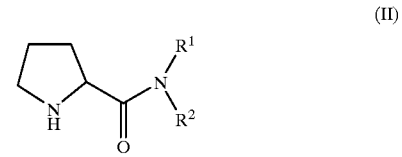

where $R^1$ and $R^2$ have the abovementioned meanings, and eliminating the group —$NR^1R^2$ by hydrolysis where appropriate the peptide obtained in this way.

9 Claims, No Drawings

PREPARATION OF ACTIVE PEPTIDES

The invention relates to a novel process for preparing specific pentapeptides and to the novel intermediates produced when the process is carried out.

BACKGROUND OF THE INVENTION

Dolastatin 15, an active peptide isolated from the sea hare *Dolabella auricularia* (G. R. Pettit et al., J. Org. Chem. 54 (1989), 6005) and structurally related synthetic peptides which are described in WO 93-23 424 are very promising novel agents, some of which are undergoing clinical testing. Since isolation from the natural source (6.2 mg from 1600 kg of sea hare) is out of the question, interest is directed at suitable synthetic processes which make the agents available in sufficient quantity and purity on the industrial scale.

Two processes have been described for preparing dolastatin 15: the elegant synthesis of G. R. Pettit et al. (J. Am. Chem. Soc. 113 (1991), 6692 and Tetrahedron 50 (1994), 12097) prepares dolastatin 15 starting from proline methyl ester hydrochloride (scheme 1).

Scheme 1

ProOMe-HCl    VII

↓

MeVal-ProOMe    VIII

↓

Val-MeVal-ProOMe    IX

↓

Me$_2$Val-Val-MeVal-ProOMe    X

↓

Me$_2$Val-Val-MeVal-ProOH    XI (XII)

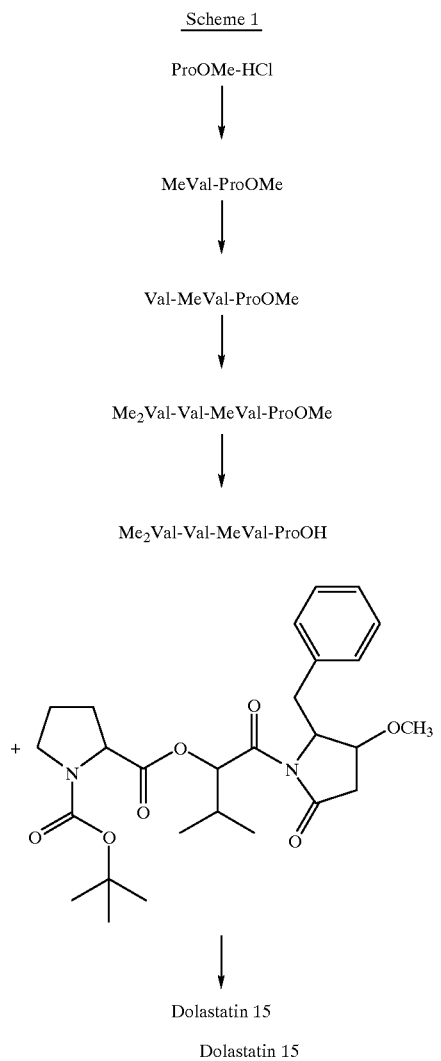

↓

Dolastatin 15

Dolastatin 15

However, the process detailed above has the following disadvantages:

1. The starting compound, proline methyl ester hydrochloride, is extremely hygroscopic. It must be prepared with careful exclusion of moisture otherwise the crystalline material deliquesces with partial ester hydrolysis. This makes industrial preparation difficult.

2. The dipeptide VIII is prone to cyclize to the diketopiperazine XIII:

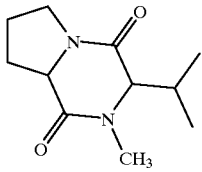

(XIII)

This cyclization leads to only small losses of yield in the laboratory but interferes considerably with the preparation of larger amounts of substance on the industrial scale.

3. Methyl esters are used to prepare each of VIII, IX and X. With the aqueous workups which are necessary at these stages, partial hydrolysis of these esters to carboxylic acids occurs. This side reaction also increases in importance on scale-up because the times during which the product is in contact with water increase when the reaction is scaled up.

4. The depsipeptide unit XII is also sensitive to hydrolysis, and it comes into contact with water twice during the isolation and preparation of the final product. The longer contact times in the industrial process lead to losses of product in this respect too.

A second process for preparing dolastatin 15 is described by Poncet et al. (Tetrahedron 48, 20, 4115–4112) starting from the tert-butyl ester of proline (scheme 2).

| | |
|---|---|
| Pro-OTBu x HCl | XIV |
| Pro-Pro-OtBu | XV |
| MeVal-Pro-Pro-OtBu | XVI |
| Val-MeVal-Pro-Pro-OtBu | XVII |
| ZVal-Val-MeVal-Pro-Pro-OtBu | XVIII |
| ZVal-Val-MeVal-Pro-Pro-OH | XIX |
| | (XX) |

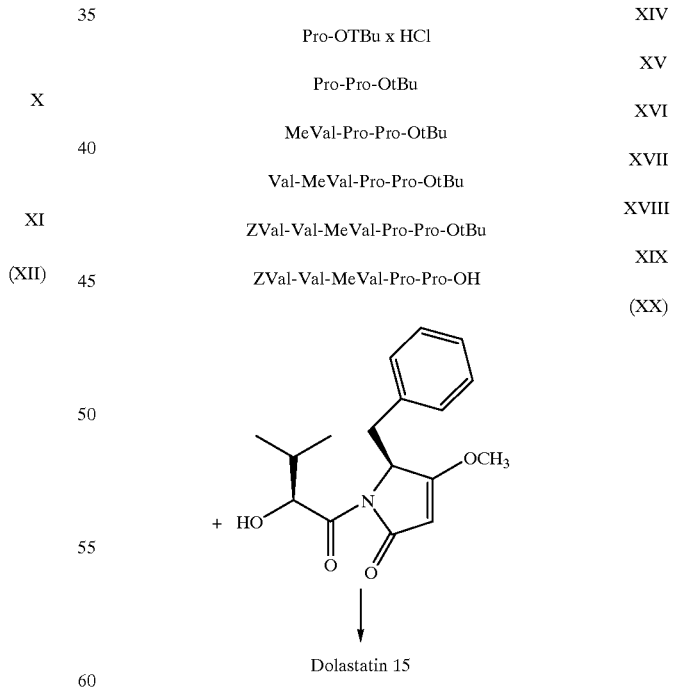

Dolastatin 15

The hydrochloride of proline tert-butyl ester is less hygroscopic than the methyl ester used in scheme 1. The dipeptide XV is somewhat less prone to form diketopiperazine than is the methyl ester VIII. The costly unit XX, which is elaborate to prepare, is employed at a later stage in the synthesis so that less of this compound is used.

The disadvantage of the Poncet process (scheme 2) is that the tert-butyl ester is more complicated to prepare than is the methyl ester. The cleavage of this ester with trifluoroacetic acid is likewise complicated, resulting in a flammable, explosive gas and fluorine-containing waste which is difficult to dispose of.

In addition, after the linkage of XIX and XX to give dolastatin 15, the Z radical must be replaced by two methyl groups (scheme 3). In this operation there is loss of a further 20% of the valuable material at a relatively late stage in the synthesis.

(XXI)

ZVal-Val-MeVal-Pro-Pro-(XX)

↓ dolastatin 15

The Pettit and Poncet processes can also be used to prepare numerous agents of WO 93/23.424 which are structurally related to dolastatin 15. For example, the tetrapeptide acid XI can be linked to proline benzylamide to give agent No. 234 from WO 93/23.424 (scheme 4).

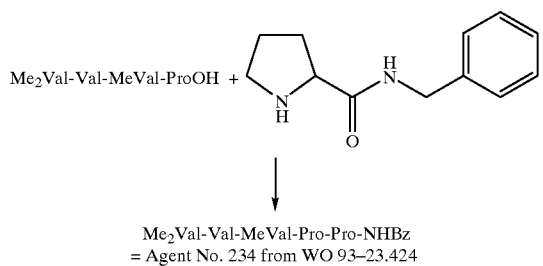

Me₂Val-Val-MeVal-Pro-Pro-NHBz
= Agent No. 234 from WO 93–23.424

The pentapeptide acid XIX from scheme 2 can be reacted in a similar manner with a dipeptide to produce the heptapeptide XXII, from which agent No. 1 from WO 93/23.424 can then be prepared (scheme 5).

ZVal-Val-MeVal-Pro-Pro-OH
XIX + Val-Phe-NH₂

↓

ZVal-Val-MeVal-Pro-Pro-Val-PheNH₂

↓

Me₂Val-Val-MeVal-Pro-Pro-Val-PheNH₂
= Agent No. 1 from WO 93/23.424

The problems described above adversely affect the yields and the industrial implementability of the peptide synthesis for preparing agents via XIX and XI.

DETAILED DESCRIPTION OF THE INVENTION

A novel process which facilitates access to the said agents and also simplifies the synthesis of the natural product dolastatin 15 has now been found.

The invention relates to a process for preparing pentapeptides of the formula I

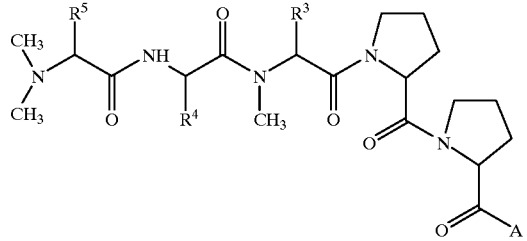

where
A is OH or $NR^1R^2$, where $R^1$ and $R^2$ are each, independently of one another, hydrogen, $C_{1-7}$-alkyl, phenyl with up to three substituents (independently of one another $C_{1-6}$-alkyl, $CF_3$, nitro, halogen) or benzyl with up to three substituents (independently of one another $C_{1-6}$-alkyl, $CF_3$, nitro, halogen), $R^3$ is ethyl, isopropyl, isobutyl, tert-butyl or 1-methylpropyl, $R^4$ is ethyl, isopropyl, isobutyl, tert-butyl or 1-methylpropyl, and $R^5$ is ethyl, isopropyl, isobutyl, tert-butyl or 1-methylpropyl, which comprises converting a prolinamide of the formula II

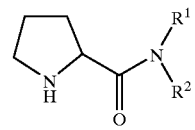

where $R^1$ and $R^2$ have the abovementioned meanings, into the dipeptide of the formula III

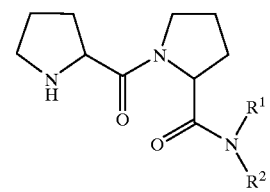

where $R^1$ and $R^2$ have the abovementioned meanings, converting the latter into the tripeptide of the formula IV

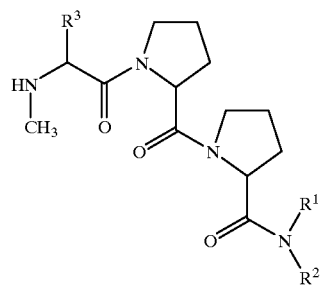

where $R^1$, $R^2$ and $R^3$ have the abovementioned meanings, converting he latter into the tetrapeptide of the formula V

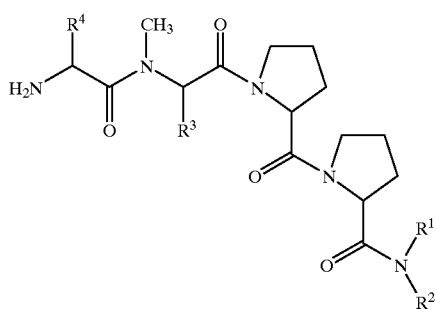

(V)

where R¹, R², R³ and R⁴ have the abovementioned meanings, and converting the latter into the pentapeptide of the formula I and, if required, hydrolyzing the resulting pentapeptide I with prolyl endopeptidase (PEP) to give the pentapeptidecarboxylic acid VI

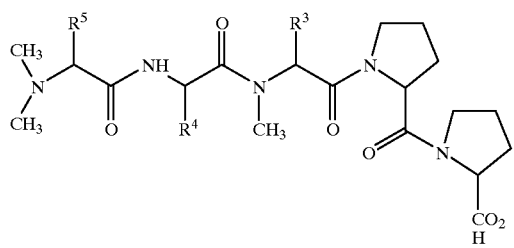

(VI)

It is characteristic of the process that it starts from prolinamides of the formula II and affords the agents I via the peptides III, IV and V.

The compounds II, III, IV, V and I can be employed as free bases. It is often advantageous to use the salts of these compounds with various acids.

Examples of suitable acids are: HCl, HBr, $H_3PO_4$, $H_2SO_4$, malonic acid, oxalic acid, fumaric acid, maleic acid, toluenesulfonic acid and methanesulfonic acid.

The compounds I and VI are disclosed in WO 93/23.424. They are valuable active peptides and can be further processed to other active substances such as the natural product dolastatin 15. For this purpose, VI is activated by conventional methods and reacted with the unit XX as described by Poncet et al. (Tetrahedron 48 (1992), 4115–4122).

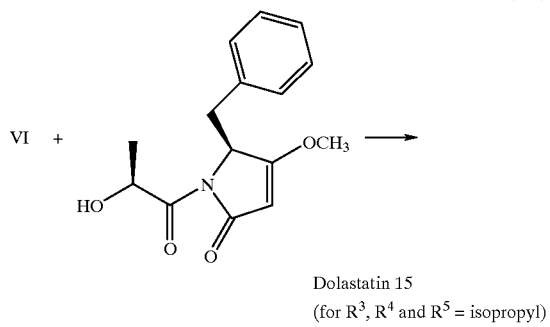

(XX)

Dolastatin 15
(for R³, R⁴ and R⁵ = isopropyl)

Further agents from WO 93/23.424 are obtained by conventional methods of peptide coupling from VI and amino acids or peptides.

The advantages of the novel process for preparing said compounds and, in particular, the natural product dolastatin 15 are the following:

The starting compounds are readily available prolinamides which are not hygroscopic even in the form of their crystalline hydrochlorides.

In the preparation of the dipeptide there is only a minor risk of formation of diketopiperazines. Both in the Pettit process and in the Poncet method of synthesis there must be expected to be formation of diketopiperazines especially with the longer contact times in an industrial synthesis.

At all coupling stages in the novel process, the terminal carboxyl group is very effectively protected as amide and can be eliminated highly specifically and simply with prolyl endopeptidase (PEP). By contrast, the methyl ester used by Pettit is partially cleaved, whereas the tert-butyl ester used by Poncet is more difficult to prepare industrially and gives rise to problems in the elimination.

The unit XX is required in the novel process only in the very last stage of the synthesis, so that less of this substance is required than in the Poncet process, which can be carried out only with great complexity.

The process according to the invention not only provides good access to dolastatin 15 but also makes it possible for numerous agents mentioned in WO 93/23.424 to be synthesized very easily. Said patent application describes the preparation of the antineoplastic peptides via a solid-phase synthesis. This method is very unsuitable for preparation on the industrial scale.

The following examples describe the process according to the invention.

Prolinamides of the structure II are prepared from proline derivatives of the formula XXI where A is an activating substituent such as methoxycarbonyl or pivaloyl and P is a protective group, eg. tert-butoxycarbonyl (BOC) or benzyloxycarbonyl (Z).

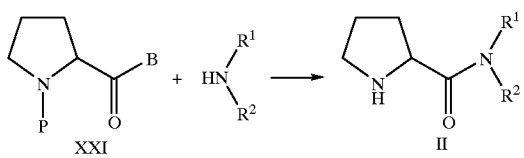

EXAMPLE 1

Proline Benzylamide Hydrochloride 48.2 g of pivaloyl chloride were added dropwise to a solution of 99.7 g of Z-proline and 58 ml of triethylamine in 1 l of $CH_2Cl_2$ at –10° C. to 15° C. The mixture was stirred at –10° C. for 45 min and then 42.8 g of benzylamine in 500 ml of $CH_2Cl_2$ were added over the course of 0.5 h at –10° C. The mixture was stirred at room temperature for 1 h. The $CH_2Cl_2$ solution was then washed twice with 500 ml of water, twice with 500 ml of 10% strength aqueous $NaHCO_3$ solution, twice with 500 ml of water, twice with 500 ml of 5% strength aqueous citric acid solution and twice with 500 ml of water, dried over $Na_2SO_4$ and evaporated. 120 g of residue remained and were taken up in 200 ml of ethyl acetate. 1.2 l of n-heptane were added to the ethyl acetate solution, the mixture was stirred for 1 h, filtered with suction and dried at 50° C. under reduced pressure. The Z-proline benzylamide obtained in this way (110 g, m.p. 93–94° C.) was dissolved in 1.5 l of methanol. 0.5 g of Pd/C (10%) was added and hydrogen was then passed in. The solution absorbed 0.5 l of $H_2$ at room temperature over the course of 1.5 h. Removal of the catalyst by filtration, and evaporation resulted in 4.6 g of a yellow oil which could be used further without further purification. High-purity product was obtained by precipitating the proline benzylamide hydrochloride. For this, 4.1 g of proline benzylamide were dissolved in 400 ml of isopropanol. 63 ml of a saturated solution of HCl in isopropanol were added, the resulting suspension was stirred at 0° C. to −5° C. for 2 h, the residue was filtered off with suction, washed twice with 250 ml of isopropanol and dried at 50° C. under reduced pressure. 4 g of proline benzylamide hydrochloride were obtained, $[\alpha]^{20}_D = -45°$.

Dipeptides of the structure III are prepared from prolinamides II and suitable proline derivatives by conventional peptide coupling methods.

EXAMPLE 2
Pro-Pro-NHBz×HCl 120.6 g of pivaloyl chloride were added dropwise over the course of 20 min to a solution of 249 g of Z-proline and 202.4 g of triethylamine in 2 l of $CH_2Cl_2$ at −5° C. to −10° C. The mixture was stirred at −55° C. for 60 min and then, at −5° C. to −10° C., a solution of 246 g of proline benzylamide hydrochloride in 300 ml of methanol was added over the course of 30 min. The mixture was stirred at below 0° C. for 1 h and at room temperature for 15 h. The solution was washed with 1 l of $H_2O$, 1 l of 10% strength acetic acid, 1 l of $H_2O$, 1 l of 10% strength NaOH and 1 l of $H_2O$. The organic phase was evaporated for drying. The residue was taken up in 1 l of methanol and refluxed for 1 h. Methanol was replaced by 2.5 l of isopropanol. 30 g of Pd/C (5%) were added and hydrogen was passed in for 4 h to saturation. 120 ml of saturated isopropanolic HCl solution were added and then the catalyst was filtered off. The mother liquor was concentrated and the residue was mixed with 400 l of isopropanol. After crystallization had started, 2 l of methyl tert-butyl ether were added. The mixture was stirred at room temperature for 15 h, filtered with suction, washed with methyl tert-butyl ether and dried under reduced pressure. Yield: 277 g (81.3%, m.p. 185.5–187° C., $[\alpha]^{20}_D = -96°$.

Tripeptides of the structure IV were prepared from the dipeptides III and suitable derivatives of N-methylamino acids (such as N-methylvaline, N-methylleucine, N-methylisoleucine, N-methyl-tert-leucine) by conventional peptide coupling methods.

EXAMPLE 3
MeVal-Pro-Pro-NHBz×HCl 636 g of a 50% strength solution of propanephosphoric anhydride in ethyl acetate were added dropwise over the course of 40 min to a solution of 199.5 g of Z-MeVal and 253 g of Pro-Pro-NHBz×HCl and 417 g of diisopropylethylamine at −5 to −10° C. The mixture was stirred at room temperature for 15 h, 1 l of water was added, and the organic phase was washed with 750 ml of 10% strength acetic acid, 750 ml of water, 750 ml of 10% strength NaOH and 750 ml of water. The organic phase was concentrated and the residue was taken up in 2.5 l of isopropanol. 90 g of Pd/C (5%) were added and then $H_2$ was passed in for 8 h. Removal of the catalyst by filtration was followed by evaporation. The residue was dissolved in 800 ml of isopropanol, 100 ml of isopropanolic HCl were added, and seeding was carried out at 45° C. After addition of 2 l of methyl tert-butyl ether, the mixture was stirred at room temperature overnight, filtered with suction, washed with isopropanol and dried. Yield 313 g (92.5%), m.p. 243–244° C., $[\alpha]^{20}_D = -141°$.

Tetrapeptides of the structure V were prepared from the tripeptides IV and suitable derivatives of the amino acids valine, α-aminobutyric acid, leucine, tert-leucine and isoleucine.

EXAMPLE 4
Val-MeVal-Pro-Pro-NHBz×HCl 94.5 g of pivaloyl chloride were added dropwise over the course of 20 min to a solution of 188.5 g of Z-valine and 151.2 g of triethylamine in 1.5 l of $CH_2Cl_2$ at −5° C. to −10° C. After stirring at −5 to −10° C. for 90 min, 337.5 g of MeVal-Pro-Pro-NHBz×HCl were added in portions over the course of 40 min at −5° C. to −10° C. The mixture was stirred at room temperature for 15 h, 750 ml of water were added, and the organic phase was washed with 750 ml of 10% strength acetic acid, 750 ml of water, 750 ml of 10% strength NaOH and 750 ml of water. The organic phase was concentrated. The residue was dissolved in 2 l of methanol and refluxed for 1 h. 30 g of Pd/C (5%) suspended in 60 ml of water were added and then hydrogen was passed in to saturation (2.5 h). The catalyst was removed by filtration and the filtrate was then evaporated to dryness. The residue was mixed with 600 ml of isopropanol and acidified with 120 ml of 30% strength isopropanolic HCl. Seeding was followed by stirring at room temperature for 15 h. 2 l of methyl tert-butyl ether were added to the mass of crystals. After stirring for 2 h, they were filtered off with suction, washed with isopropanol and dried. 306 g were obtained (74.1% yield), m.p. 205–208.5° C., $[\alpha]^{20}_D = -179.5°$.

Pentapeptides of the structure I were prepared from the tetrapeptides and suitable derivatives of the amino acids valine, α-aminoisobutyric acid, leucine, tert-leucine and isoleucine. The terminal methyl groups could be introduced after the coupling to give the pentapeptide. It is also possible as an alternative to use suitable derivatives of N,N-dimethylvaline, N,N-dimethyl-aminoisobutyric acid, N,N-dimethylleucine, N,N-dimethyl-tert-leucine and N,N-dimethylisoleucine.

EXAMPLE 5
$Me_2$Val-Val-MeVal-Pro-Pro-NHBz×HCl (Agent No. 234 from WO 93/23.424)

42.4 g of a 50% strength solution of propanephosphoric anhydride in ethyl acetate were added dropwise over the course of 20 min to a solution of 8.7 g of N,N-dimethylvaline, 27.4 g of Val-MeVal-Pro-Pro-NHBz×HCl and 21.6 g of triethylamine in 100 ml of $CH_2Cl_2$ at 0 to −6° C. The mixture was stirred in the cold for 1 h and at room temperature overnight. The organic phase was washed with 50 ml of water and concentrated. The residue was dissolved in 50 ml of isopropanol and acidified with 10 ml of 30% strength isopropanolic HCl. Seeding was carried out, 150 ml of methyl tert-butyl ether were added at 60° C., and the mixture was stirred overnight, filtered with suction, washed with isopropanol and dried. 29.9 g were obtained (88.3% yield) $[\alpha]^{20}_D = -180.3°$ C.

The pentapeptide acids VI were obtained from the pentapeptide amides V by hydrolysis with prolyl endopeptidase (T. Yoshimoto et al., J. Biol. Chem., 255 (1980), 4786, J. Biochem. 110 (1991), 873). Particularly suitable substrates in this connection are the benzylamides. Alkylamides can also be hydrolyzed, but react considerably more slowly.

The pentapeptidecarboxylic acid VI a=$Me_2$Val-Val-MeVal-Pro-ProOH is the suitable precursor for the natural product dolastatin 15. For this, VI a must be coupled to the hydroxy amide XX. A suitable synthesis of XX is described by J. Poncet et al. in Tetrahedron 48 (1992) 4115–4122.

EXAMPLE 6
Preparation of dolastatin 15

A solution of 2.4 g of isopropenyl chloroformate in 20 ml of methylene chloride was added dropwise to a solution of 6 g of VI a, 3.0 g of XX, 2.0 g of DMAP and 2.0 g of triethylamine in 150 ml of dimethyl chloride at 0° C. The mixture was stirred at 0° C. for 15 min and at room temperature for 4 h. It was washed with water, 5% strength aqueous NaHCO₃ solution and water, dried over Na₂SO₄ and concentrated. The residue was dissolved in hexane/ethyl acetate and chromatographed on silica gel. Yield: 5.8 g of amorphous solid.

We claim:

1. A process for preparing a pentapeptide of the formula I

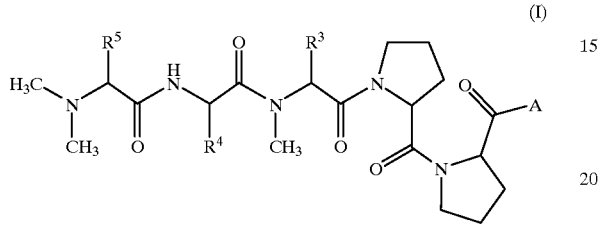
(I)

where

A is OH or $NR^1R^2$, where $R^1$ and $R^2$ are each, independently of one another, hydrogen, $C_{1-7}$-alkyl, phenyl which is unsubstituted or carries up to three substituents selected from the group of alkyl, $CF_3$, nitro and halogen, or benzyl which is unsubstituted or carries up to three substituents selected from the group of alkyl, $CF_3$, nitro and halogen, $R^3$ is ethyl, isopropyl, isobutyl, tert-butyl or 1-methylpropyl, $R^4$ is ethyl, isopropyl, isobutyl, tert-butyl or 1-methylpropyl, and $R^5$ is ethyl, isopropyl, isobutyl, tert-butyl or 1-methylpropyl, wherein said process comprises (a) converting a prolinamide of the formula II

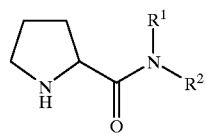
(II)

into the dipeptide of the formula III

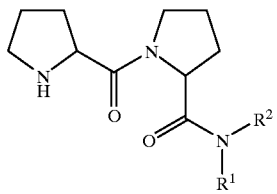
(III)

(b) converting the dipeptide of the formula III into the tripeptide of the formula IV

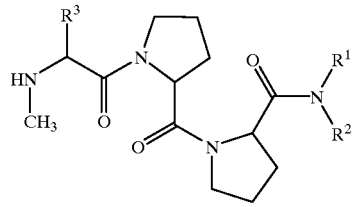
(IV)

(c) converting the tripeptide of the formula IV into the tetrapeptide of the formula V

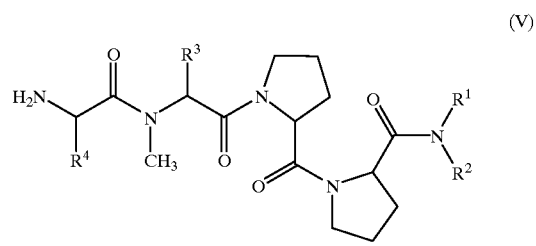
(V)

and (d) converting the tetrapeptide of the formula V into the pentapeptide of the formula I wherein A is $NR^1R^2$, and, if required, (e) hydrolyzing the resulting pentapeptide I with propyl endopeptidase (PEP) to give the pentapeptidecarboxylic acid VI

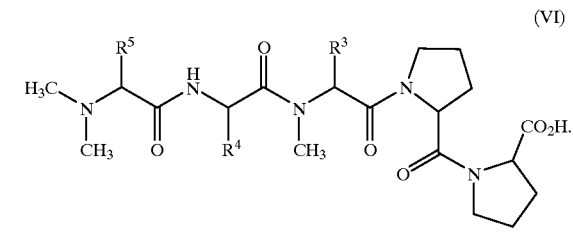
(VI)

2. The process defined in claim 1, wherein the substances of the formulae II, III, IV, V and I are in the form of their salts.

3. The process defined in claim 1, wherein $R^1$ is benzyl which is unsubstituted or carries up to three substituents selected from the group of alkyl, $CF_3$, nitro and halogen.

4. The process defined in claim 1, wherein $R_2$ is hydrogen.

5. An intermediate having the formula IV

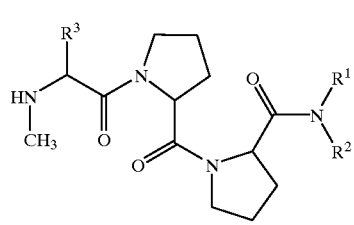
(IV)

or the formula V,

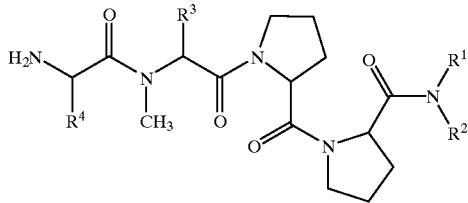

(V)

where

R¹ and R² are each, independently of one another, hydrogen, $C_{1-7}$-alkyl, phenyl which is unsubstituted or carries up to three substituents selected from the group of alkyl, $CF_3$, nitro and halogen, or benzyl which is unsubstituted or carries up to three substituents selected from the group of alkyl, $CF_3$, nitro and halogen, $R^3$ is ethyl, isopropyl, isobutyl, tert-butyl or 1-methylpropyl.

$R^4$ is ethyl, isopropyl, isobutyl, tert-butyl or 1-methylpropyl.

6. The intermediate of the formula IV defined in claim 5, wherein $R^1$ is benzyl which is unsubstituted or carries up to three substituents selected from the group of alkyl, $CF_3$, nitro and halogen.

7. The intermediate of the formula IV defined in claim 5, wherein $R^2$ is hydrogen.

8. The intermediate of the formula V defined in claim 5, wherein $R^1$ is benzyl which is unsubstituted or carries up to three substituents selected from the group of alkyl, $CF_3$, nitro and halogen.

9. The intermediate of the formula V defined in claim 5, wherein $R^2$ is hydrogen.

* * * * *